United States Patent
Verbeck

(10) Patent No.: US 6,340,368 B1
(45) Date of Patent: Jan. 22, 2002

(54) IMPLANTABLE DEVICE WITH RADIOPAQUE ENDS

(75) Inventor: Marcel A. E Verbeck, Heerlen (NL)

(73) Assignee: Medtronic Inc., Minneapolis, MN (US)

(*) Notice: Subject to any disclaimer, the term of this patent is extended or adjusted under 35 U.S.C. 154(b) by 0 days.

(21) Appl. No.: 09/178,397

(22) Filed: Oct. 23, 1998

(51) Int. Cl.⁷ .................................................. A61F 2/00
(52) U.S. Cl. ..................................................... 623/1.34
(58) Field of Search ................................. 623/1, 11, 12, 623/1.34

(56) References Cited

U.S. PATENT DOCUMENTS

| | | |
|---|---|---|
| 269,882 A | 1/1883 | Reed |
| 308,368 A | 11/1884 | McGill |
| 3,618,614 A | 11/1971 | Flynn |
| 3,757,768 A | 9/1973 | Kline |
| 4,202,349 A | 5/1980 | Jones |
| 4,279,252 A | 7/1981 | Martin |
| 4,345,602 A | 8/1982 | Yoshimura et al. |
| 4,430,086 A | 2/1984 | Ganz et al. |
| 4,456,017 A | 6/1984 | Miles |
| 4,464,176 A | 8/1984 | Wijayarathna |
| 4,469,483 A | 9/1984 | Becker et al. |
| 4,538,622 A | 9/1985 | Samson et al. |
| 4,545,390 A | 10/1985 | Leary |
| 4,577,637 A | 3/1986 | Mueller, Jr. |
| 4,588,399 A | 5/1986 | Nebergall et al. |
| 4,617,932 A | 10/1986 | Kornberg |
| 4,619,274 A | 10/1986 | Morrison |
| 4,636,346 A | 1/1987 | Gold et al. |
| 4,657,024 A | 4/1987 | Coneys |
| 4,662,404 A | 5/1987 | LeVeen et al. .............. 138/120 |
| 4,721,117 A | 1/1988 | Mar et al. |
| 4,757,827 A | 7/1988 | Buchbinder et al. |
| 4,763,647 A | 8/1988 | Gambale |
| 4,793,359 A | 12/1988 | Sharrow |
| 4,796,637 A | 1/1989 | Mascuch et al. |
| 4,798,598 A | 1/1989 | Bonello et al. |

(List continued on next page.)

FOREIGN PATENT DOCUMENTS

| | | |
|---|---|---|
| EP | 0 146 699 | 7/1985 |
| EP | 0 480 667 | 4/1992 |
| EP | 0 508 473 | 10/1992 |
| EP | 0 517 075 | 12/1992 |
| EP | 0 519 214 | 12/1992 |
| EP | 0 519 604 | 12/1992 |
| EP | 0 649 637 | 4/1995 |
| EP | 0 669 114 | 8/1995 |
| EP | 0 679 372 | 11/1995 |
| EP | 0 680 734 | 11/1995 |
| EP | 0 684 022 | 11/1995 |
| EP | 0 686 379 | 12/1995 |
| EP | 0 699 423 | 3/1996 |
| EP | 0 709 068 | 5/1996 |
| EP | 0 805 653 | 7/1998 |

(List continued on next page.)

OTHER PUBLICATIONS

U.S. Appl. No. 09/046,241 entitled "Catheter Having Extruded Radiopaque Stripes Embedded in Soft Tip and Method of Fabrication".

Primary Examiner—Michael J. Milano
(74) Attorney, Agent, or Firm—Sterne, Kessler, Goldstein & Fox, PLLC

(57) ABSTRACT

The present invention provides an implantable device for use in the treatment of at least partially obstructed body lumen. The implantable medical device includes at least one radiopaque tubular section attached to a first end of a tubular midsection. Upon viewing the device with x-ray, a three dimensional image is visible that allows for increased accuracy in assessing device placement, device sizing, device deployment, and even lumen orientation.

16 Claims, 3 Drawing Sheets

U.S. PATENT DOCUMENTS

| | | |
|---|---|---|
| 4,815,478 A | 3/1989 | Buchbinder et al. |
| 4,817,613 A | 4/1989 | Jaraczewski et al. |
| 4,821,722 A | 4/1989 | Miller et al. |
| 4,846,186 A | 7/1989 | Box et al. |
| 4,867,174 A | 9/1989 | Skribiski |
| 4,873,983 A | 10/1989 | Winters |
| 4,884,579 A | 12/1989 | Engelson |
| 4,886,062 A | 12/1989 | Wiktor ........................ 128/343 |
| 4,895,168 A | 1/1990 | Machek |
| 4,898,591 A | 2/1990 | Jang et al. |
| 4,906,244 A | 3/1990 | Pinchuk et al. |
| 4,922,924 A | 5/1990 | Gambale et al. |
| 4,938,220 A | 7/1990 | Mueller, Jr. |
| 4,957,110 A | 9/1990 | Vogel et al. |
| 4,981,470 A | 1/1991 | Bombeck, IV |
| 4,990,138 A | 2/1991 | Bacich et al. |
| 5,034,005 A | 7/1991 | Appling |
| 5,040,543 A | 8/1991 | Badera et al. |
| 5,045,072 A | 9/1991 | Castillo et al. |
| 5,063,935 A | 11/1991 | Gambale |
| 5,065,769 A | 11/1991 | de Toledo |
| 5,069,217 A | 12/1991 | Fleischhacker, Jr. |
| 5,081,997 A | 1/1992 | Bosley, Jr. et al. |
| 5,084,022 A | 1/1992 | Claude |
| 5,095,915 A | 3/1992 | Engelson |
| 5,105,818 A | 4/1992 | Christian et al. |
| RE33,911 E | 5/1992 | Samson et al. |
| 5,129,890 A | 7/1992 | Bates et al. |
| 5,144,959 A | 9/1992 | Gambale et al. |
| 5,147,315 A | 9/1992 | Weber |
| 5,147,317 A | 9/1992 | Shank et al. |
| 5,151,105 A | 9/1992 | Kwan-Gett |
| 5,160,559 A | 11/1992 | Scovil et al. |
| 5,171,232 A | 12/1992 | Castillo et al. |
| 5,174,302 A | 12/1992 | Palmer |
| 5,176,149 A | 1/1993 | Grenouillet |
| 5,178,158 A | 1/1993 | de Toledo |
| 5,184,627 A | 2/1993 | de Toledo |
| 5,209,730 A | 5/1993 | Sullivan |
| 5,211,636 A | 5/1993 | Mische |
| 5,221,270 A | 6/1993 | Parker |
| 5,228,453 A | 7/1993 | Sepetka |
| 5,234,416 A | 8/1993 | Macauley et al. |
| 5,250,034 A | 10/1993 | Appling et al. |
| 5,253,653 A | 10/1993 | Daigle et al. |
| 5,256,158 A | 10/1993 | Tolkoff et al. |
| 5,259,393 A | 11/1993 | Corso, Jr. et al. |
| 5,267,574 A | 12/1993 | Viera et al. |
| 5,275,622 A | 1/1994 | Lazarus et al. |
| 5,300,025 A | 4/1994 | Wantink |
| 5,300,048 A | 4/1994 | Drewes, Jr. et al. |
| 5,342,348 A | 8/1994 | Kaplan ................... 604/891.1 |
| 5,366,442 A | 11/1994 | Wang et al. |
| 5,366,473 A * | 11/1994 | Winston ........................ 623/1 |
| 5,366,504 A | 11/1994 | Andersen et al. |
| 5,387,235 A | 2/1995 | Chuter |
| 5,403,292 A | 4/1995 | Ju |
| 5,405,004 A | 4/1995 | Vest et al. |
| 5,419,324 A | 5/1995 | Dillow |
| 5,429,597 A | 7/1995 | Demello et al. |
| 5,429,617 A | 7/1995 | Hammersmark et al. |
| 5,456,251 A | 10/1995 | Fiddian-Green |
| 5,456,705 A | 10/1995 | Morris |
| 5,458,639 A | 10/1995 | Tsukashima et al. |
| 5,464,438 A | 11/1995 | Menaker |
| 5,470,315 A | 11/1995 | Adams |
| 5,476,508 A | 12/1995 | Amstrup |
| 5,480,383 A | 1/1996 | Badaoisan et al. |
| 5,484,418 A | 1/1996 | Quiachon et al. |
| 5,485,667 A | 1/1996 | Kleshinski |
| 5,489,277 A | 2/1996 | Tolkoff et al. |
| 5,489,295 A | 2/1996 | Piplani et al. |
| 5,509,910 A | 4/1996 | Lunn |
| 5,542,937 A | 8/1996 | Chee et al. |
| 5,545,138 A | 8/1996 | Fugoso et al. |
| 5,545,151 A | 8/1996 | O'Connor et al. |
| 5,549,552 A | 8/1996 | Peters et al. |
| 5,562,726 A | 10/1996 | Chuter |
| 5,562,728 A | 10/1996 | Lazarus et al. |
| 5,569,221 A | 10/1996 | Houser et al. |
| 5,571,089 A | 11/1996 | Crocker |
| 5,575,817 A * | 11/1996 | Martin ........................ 623/1 |
| 5,582,619 A | 12/1996 | Ken ........................ 606/191 |
| 5,584,821 A | 12/1996 | Hobbs et al. |
| 5,599,325 A | 2/1997 | Ju et al. |
| 5,599,326 A | 2/1997 | Carter |
| 5,603,991 A | 2/1997 | Kupiecki et al. |
| 5,609,629 A | 3/1997 | Fearnot et al. .................. 623/1 |
| 5,658,263 A | 8/1997 | Dang et al. |
| 5,662,675 A * | 9/1997 | Polanskyj Stockert ......... 623/1 |
| 5,683,370 A | 11/1997 | Luther et al. |
| 5,683,451 A | 11/1997 | Lenker et al. |
| 5,690,120 A | 11/1997 | Jacobsen et al. |
| 5,718,724 A | 2/1998 | Goicoechea et al. |
| 5,725,513 A | 3/1998 | Ju et al. |
| 5,725,572 A * | 3/1998 | Lam .............................. 623/1 |
| 5,728,042 A | 3/1998 | Schwager |
| 5,741,327 A * | 4/1998 | Frantzen .................... 623/1.37 |
| 5,769,819 A | 6/1998 | Schwab et al. |
| 5,769,830 A | 6/1998 | Parker |
| 5,769,882 A | 6/1998 | Fogarty et al. |
| 5,776,180 A | 7/1998 | Goicoechea et al. |
| 5,811,043 A | 9/1998 | Horrigan et al. |
| 5,824,037 A | 10/1998 | Fogarty et al. |
| 5,824,041 A | 10/1998 | Lenker et al. |
| 5,824,042 A | 10/1998 | Lombardi et al. |
| 5,827,225 A | 10/1998 | Ma Schwab |
| 5,853,400 A | 12/1998 | Samson |
| 5,871,468 A | 2/1999 | Kramer et al. |
| 5,876,376 A | 3/1999 | Schwab et al. |
| 5,891,112 A | 4/1999 | Samson |
| 6,024,763 A | 2/2000 | Lenker et al. |
| 6,068,622 A | 5/2000 | Sater et al. |
| 6,126,685 A | 10/2000 | Lenker et al. |
| 6,179,811 B1 | 1/2001 | Fugoso et al. |

FOREIGN PATENT DOCUMENTS

| | | | |
|---|---|---|---|
| EP | 1 004 327 | 5/2000 | |
| WO | WO 90/15582 | 12/1990 | |
| WO | WO 91/15254 | 10/1991 | |
| WO | WO 92/19151 | 11/1992 | |
| WO | WO 93/08862 | 5/1993 | |
| WO | WO 93/19663 | 10/1993 | |
| WO | WO 95/03010 | 2/1995 | |
| WO | WO 95/08966 | 4/1995 | |
| WO | WO 95/15780 | 6/1995 | |
| WO | WO 95/21592 | 8/1995 | |
| WO | 0 421 729 | 1/1996 | .......... A61M/29/00 |
| WO | WO 96/08208 | 3/1996 | |
| WO | WO 97/33534 | 9/1997 | .............. A61F/2/06 |
| WO | WO 99/17829 | 4/1999 | |

* cited by examiner

IMPLANTABLE DEVICE WITH RADIOPAQUE ENDS

FIELD OF THE INVENTION

The present invention relates to an implantable medical device and, more particularly, an implantable stent that includes substantially radiopaque ends and a method of using the same in the prevention of restenosis.

BACKGROUND OF THE INVENTION

Stenosis is a narrowing or constriction of a duct or canal. A variety of disease processes, such as atherosclerotic lesions, immunological reactions, congenital abnormalities, and the like, can lead to stenosis of arteries or ducts. In the case of stenosis of a coronary artery, this typically leads to myocardial ischema. Percutaneous transluminal coronary angioplasty (PTCA), the insertion and inflation of a balloon catheter into a stenotic vessel to affect its repair is widely accepted as an option in the treatment of obstructive coronary artery disease. In general, PTCA is used to increase the lumen diameter of a coronary artery partially or totally obstructed by a build-up of cholesterol fats or atherosclerotic plaque. Typically a first guidewire of about 0.038 inches in diameter is steered through the vascular system to the site of therapy. A guiding catheter, for example, can then be advanced over the first guidewire to a point just proximal of the stenosis. The first guidewire is then removed. A balloon catheter on a smaller 0.014 inch diameter second guidewire is advanced within the guiding catheter to a point just proximal of the stenosis. The second guidewire is advanced into the stenosis, followed by the balloon on the distal end of the catheter. The balloon is inflated causing the site of the stenosis to widen. The dilatation of the occlusion, however, can form flaps, fissures and dissections which threaten reclosure of the dilated vessel or even perforations in the vessel wall.

Other vascular invasive therapies include atherectomy (mechanical systems to remove plaque residing inside an artery), laser ablative therapy and the like. While the stenosis or occlusion is greatly reduced using these therapies, including PTCA, many patients experience a reoccurrence of the stenosis over a relatively short period. Restenosis, defined angiographically, is the recurrence of a 50% or greater narrowing of a luminal diameter at the site of a prior coronary artery disease therapy, such as a balloon dilatation in the case of PTCA therapy. Additionally, researchers have found that angioplasty or placement of a stent in the area of the stenosis irritates the blood vessel causing rapid reproduction of the inner layer of blood vessel cells and restenosis through a mechanism called hyperplasia. Restenosis is a major problem which limits the long-term efficacy of invasive coronary disease therapies. In particular, an intraluminal component of restenosis develops near the end of the healing process initiated by vascular injury, which then contributes to the narrowing of the luminal diameter. This phenomenon is sometimes referred to as "intimal hyperplasia." In some instances, restenosis develops so rapidly that it may be considered a form of accelerated atherosclerosis induced by injury. Additionally, the rapid onset of restenosis is compounded by the lack of predictability to determine which patients, vessels, or lesions will undergo restenosis.

Although the mechanism of restenosis is not fully understood, clinical evidence suggests that restenosis results from a migration and rapid proliferation of a subset of predominately medially derived smooth muscle cells which is apparently induced by the injury caused by the invasive therapy. Such injury, for example, is caused by the angioplasty procedure when the balloon catheter is inflated and exerts pressure against the artery wall, resulting in media tearing. It is known that smooth muscle cells proliferate in response to mechanical stretch and stimulation by a variety of growth factors. It is believed that such proliferation stops one to two months after the initial invasive therapy procedure but that these cells continue to express an extracellular matrix of collagen, elastin and proteoglycans. Additionally, animal studies have shown that after balloon injury, denudation of endothelial cells occurs, followed by platelet adhesion and aggregation, and the release of platelet-derived growth factor (PDGF) as well as other growth factors. As mentioned above, this mass of tissue contributes in the re-narrowing of the vascular lumen in patients who have restenosis. It is believed that a variety of biologic factors are involved in restenosis, such as the extent of the injury, platelets, inflammatory cells, growth factors, cytokines, endothelial cells, smooth muscle cells, and extracellular matrix production, to name a few.

Implantable devices are known for use in the prevention of restenosis. Typically, such implantable devices are intra-arterial stents fabricated from either a pure metal or a metal alloy. In general, a biocompatible metal stent props open blocked coronary arteries, keeping them from reclosing after balloon angioplasty. For example, a stent is described by Wiktor in U.S. Pat. No. 4,886,062, wherein the stent includes metal elements made of wire loops in a wound structure which allows individual loops to move with respect to one another. Another stent is described by Wolff in published European Patent Application No. 0421729, wherein the stent includes metal elements made of individual stent segments joined together by hinges.

These stents can then be deployed in a body lumen by means appropriate to their design. First, a balloon of appropriate size and pressure is first used to open the lesion. Then, for example, in the case of the stent described by Wiktor, the process is repeated with a stent crimped on a second balloon. The second balloon may be a high pressure type of balloon, e.g., more than 12 atmospheres, to insure that the stent is fully deployed upon inflation. The stent is deployed when the balloon is inflated. The stent remains as a permanent scaffold after the balloon is withdrawn. A high pressure balloon is preferable for stent deployment because the stent must be forced against the artery's interior wall so that it will fully expand thereby precluding the ends of the stent from hanging down into the channel encouraging the formation of thrombus.

Thus, there is a continuing need for improved implantable devices that can be used in preventing restenosis. In particular, it would be desirable to provide an implantable device that can be easily and accurately inserted into even very small vessels and which accurately center the source in the vessel while permitting effective perfusion so that treatment can be conducted over reasonably long periods.

SUMMARY OF THE INVENTION

It is an object of the invention to provide an implantable device for preventing restenosis. It is also an object of the present invention to provide an implantable device that can be easily and accurately deployed in a body lumen by providing a visible means to assess deployment and placement of the implantable device. It is a further object of the present invention to provide an implantable device having longitudinal flexibility which allows it to conform to curves and variations within a body lumen and thus is less traumatic to the in vivo implantation site.

These and other objects have been accomplished by the implantable device of the present invention. One aspect of the present invention provides an implantable medical device including a radiolucent midsection tubular structure having a first end and a second end, the midsection tubular structure being expandable from an initial diameter to a second diameter; and a first tubular structure attached to the first end of the midsection tubular structure, the first tubular structure being expandable from an initial diameter to a second diameter to provide a substantially uninterrupted passageway therethrough, wherein the first tubular structure comprises a substantially radiopaque material.

Another aspect of the present invention provides an implantable medical device including a midsection tubular structure having a first end and a second end, the midsection tubular structure being expandable from an initial diameter to a second diameter, wherein the midsection is formed from a substantially radiolucent material. The implantable device also includes a first tubular structure attached to the first end of the midsection tubular structure, the first tubular structure being expandable from an initial diameter to a second diameter; and a second tubular structure attached to the second end of the midsection tubular structure, the second tubular structure being expandable from an initial diameter to a second diameter to provide a substantially uninterrupted passageway from the first tubular structure to the second tubular structure, wherein the first and the second tubular structure each consist essentially of a substantially radiopaque material.

Preferably, the substantially radiopaque material is more compliant than the substantially radiolucent material. Typically, the radiopaque material has a density of about 19.3 gm/cm$^3$ to about 21.0 gm/cm$^3$.

The radiopaque material is preferably selected from the group consisting of tantalum, gold, iridium, and a combination thereof, whereas the radiolucent material is preferably selected from the group of stainless steel, niobium, titanium, and a combination thereof.

Preferably, in one embodiment, the first tubular structure comprises less than about 25% of a total length of the implantable device. Preferably, in another embodiment, the first tubular structure and the second tubular structure each comprise about 20% to about 15% of a total length of the implantable device.

Yet another aspect according to the present invention provides a method for the treatment of restenosis which includes placing an implantable device having an initial diameter on a catheter suitable for delivery in a body lumen to form a catheter/device assembly. Preferably, the implantable device includes an expandable midsection tubular structure having a first end and a second end; and an expandable first tubular structure attached to the first end of the midsection tubular structure, wherein the first tubular structure comprises a substantially radiopaque material. The method also includes the steps of delivering the catheter/device assembly to an at least partially obstructed in vivo lumen location; inflating the catheter to expand the implantable medical device from the initial diameter to a second diameter; and withdrawing the catheter. A method according to the present invention may also include the step of evaluating the in vivo location of the implantable device by exposure to x-ray such that the expandable first tubular structure and the expandable second tubular structure are visible.

DETAILED DESCRIPTION OF THE PREFERRED EMBODIMENTS

Figure 1:
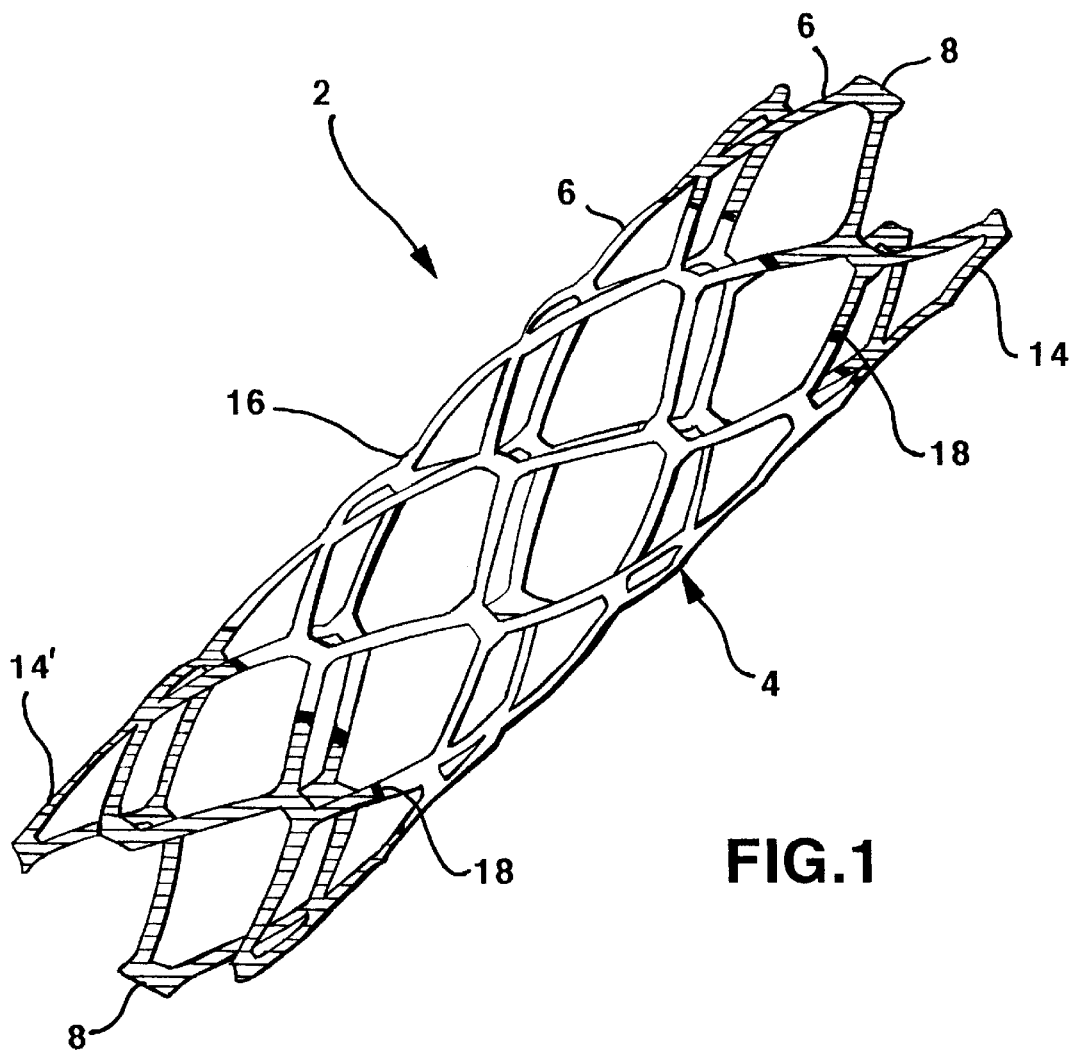
FIG. 1 is an enlarged perspective view of one embodiment of the present invention prior to implantation.

The present invention provides an implantable device for treating body lumens particularly in the prevention of restenosis of veins and/or arteries following dilation of stenoic segments. Also provided is a method for preventing restenosis utilizing an implantable device described herein.

According to the present invention, an implantable device includes a tubular structure having an initial diameter and being expandable from the initial diameter to an enlarged diameter. An initial diameter is preferably less than about 2 mm for most vascular applications, more preferably from about 1.25 mm to about 2 mm, and most preferably from about 1.00 mm to about 1.5 mm. One skilled in the art will readily appreciate that an enlarged diameter will be determined based on the inner diameter of the lumen to be treated with an implantable device according to the present invention. Typically, for cardiovascular applications, the enlarged diameter will be from about 2 mm to about 6 mm, and more typically from about 2 mm to about 4 mm.

The implantable device is preferably in a tubular or cylindrical shape, as mentioned above. An implantable device in accordance with the present invention preferably includes two portions: a radiolucent midsection and at least one substantially radiopaque end attached to the radiolucent midsection to provide a substantially uninterrupted passageway therethrough.

Preferably, the at least one substantially radiopaque end accounts for less than about 25% of a total length of the implantable device. More preferably, at least one substantially radiopaque end accounts for about 20% to about 15% of a total length of the implantable device.

Preferably, the radiolucent midsection is formed of a biocompatible material that will generally have a non-elastic property in that it will retain its shape following expansion. This provides a means for increased control of the body lumen expansion. In operation, the outward force applied from the interior of the implantable device will increase the diameter of the tubular member 4. The degree of radial expansion can be controlled by the amount of force exerted within the tubular member 4. For example, angioplasty balloon catheters provide a means for controlling the force and, therefore, the expansion of the tubular member, as will be discussed in greater detailed below. The radiolucent midsection 16 can be formed from such materials as stainless steel, niobium, and titanium, to name a few.

An implantable device also includes at least one, preferably two, substantially radiopaque end including, and more preferably, consisting essentially of a substantially radiopaque material. Preferred substantially radiopaque materials are those that have a density of about 19.3 gm/cm$^3$ to about 21.0 gm/cm$^3$. Preferred materials are typically a metal or a metal alloy. Suitable metals can be selected from the group of tantalum, gold, and iridium, to name a few. A suitable metal alloy can be selected from the group of a platinum-iridium alloy that can include, for example, 90% platinum and 10% iridium. A particularly preferred substantially radiopaque material is tantalum.

Additionally, the tubular member may be coated with a biologically inert coating such as porous polyurethane and the like. If present, the biologically inert coating should be thin enough and possess sufficient elasticity so as not to interfere with the expansion property of the implantable device. If present, the coating may also include an anchoring means for securing the implantable device to the inner wall of the body lumen. Such anchoring means may include projections which extend radially outward from an outer surface of the tubular member toward the inner wall of the body lumen.

Depending upon the in vivo placement of an implantable device in accordance with the present invention, it may be desired to provide an implantable device that includes substantially radiopaque materials having certain characteristics with a radiolucent material having different characteristics. For example, it may be desired to have a radiolucent material that is relatively less compliant that the substantially radiopaque material used at either end. In this configuration, a midsection including the less compliant radiolucent material may fully support an obstructed body lumen, for example to maintain an open stenosis, whereas the more compliant substantially radiopaque ends may cause less damage to the surrounding, likely healthy, body lumen tissue. In this regard, the more compliant substantially radiopaque ends may prevent further complications such as undesired bleeding, restenosis, etc., at the device ends. Thus, protection of the healthy surrounding tissue is accomplished by the inclusion of a more compliant material in the device ends rather than by varying the geometry of the device. Accordingly, an implantable device in accordance with the present invention preferably includes more than one type of material but has a substantially uniform geometry prior to implantation.

Referring to FIG. 1, a perspective view of one embodiment of a stent 2 in accordance with the present invention is shown. The stent 2 includes a tubular member 4 that is formed from longitudinal elements 6 joined to form a tubular configuration by horizontal elements 8. Perforations 10 are formed by spaces between the longitudinal elements 6 and horizontal elements 8. The tubular member 4 defines an interior 12 of the stent 2. As shown in FIG. 1, the stent 2 has an initial diameter prior to implantation which will then expanded to a second diameter once implanted.

The stent 2 also includes a radiolucent midsection 16 having a first substantially radiopaque end 14 and a second substantially radiopaque end 14' attached on either side thereof via a plurality of attachment points 18. The exact number of attachment points will depend upon the number of longitudinal elements of the radiolucent midsection and the corresponding number of longitudinal elements of a substantially radiopaque end which need to be joined to complete the structure.

Figure 2:
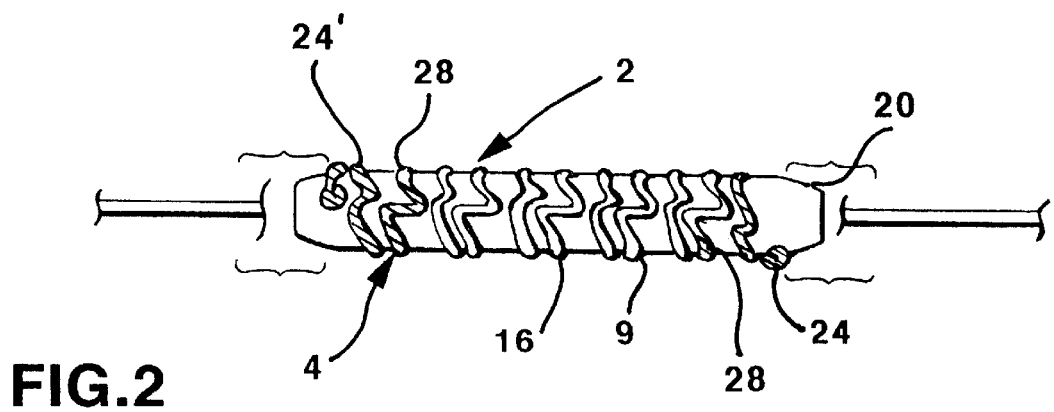
FIG. 2 is an enlarged perspective view of another embodiment of the present invention in preparation of implantation.

Referring to FIG. 2, a perspective view of another embodiment of a stent 2' in accordance with the present invention is shown. The stent 2' includes a tubular member that is formed from a helically wound element 8. The helically wound element 9 is initially preformed into a two-dimensional zig-zag form, thus creating a flat expandable band. The zig-zag pattern can vary as to its shape and tightness of the angles forming the pattern. In order to create an implantable device such as a stent, and to have it assume an initial configuration (i.e., having an initial diameter) as shown in FIG. 2, a length of the preformed band is wrapped or helically coiled on a suitable mandrel 20. Typically, care is taken to form the band flat around the mandrel 20 with little or no tension to prevent premature linear expansion of the band. This produces a stent having a tubular or cylindrical shape which permits flexing of the tubular member 4 along it longitudinal axis.

As mentioned with respect to FIG. 1, the stent 2' shown in FIG. 2 also includes a radiolucent midsection 16' having a first substantially radiopaque end 24 and a second substantially radiopaque end 24' attached on either side thereof via an attachment point 28. Because the tubular member is formed from a single helically wound element, each substantially radiopaque end can be joined to a radiolucent end with only a single attachment point.

It will be appreciated by one with skill in the art that although the present invention has been shown with element configurations described in FIG. 1 and FIG. 2, other configurations are suitable for use in the present invention, such as those described by Wiktor in U.S. Pat. No. 4,886,062, and by Wolff in published European Patent Application No. 0421729.

In any embodiment of the present invention, a substantially radiopaque end and a radiolucent midsection can be attached by any conventional method such as by welding, brazing, or otherwise mechanically bonding the substantially radiopaque material to the radiolucent material. One with ordinary skill in the art will readily appreciate that each substantially radiopaque end of a given implantable device can be made of the same or a different substantially radiopaque material. One preferred embodiment of the present invention provides a stent that includes a radiolucent midsection formed from stainless steel and a first substantially radiopaque end and a second substantially radiopaque end, wherein in each substantially radiopaque end is formed from tantalum.

Figure 3A:
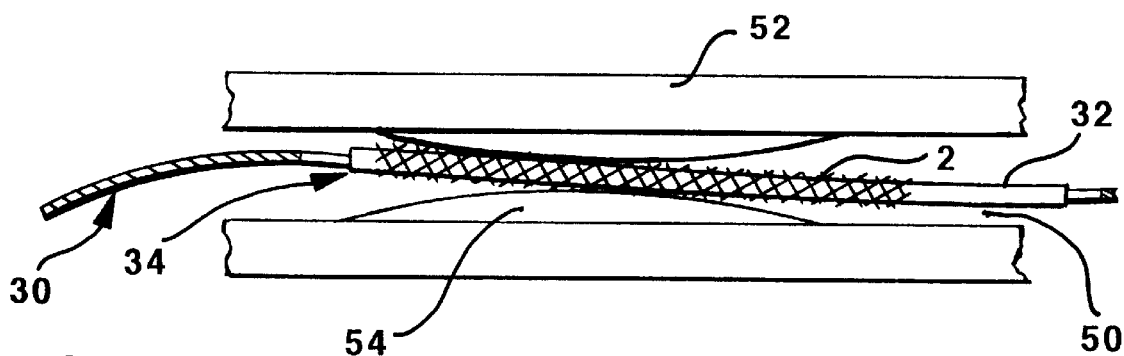
FIGS. 3A–3C illustrate a method of the present invention for in vivo positioning an implantable device of the present invention.

In FIG. 3A it is shown how a catheter/stent assembly 34, emanating from a guiding catheter 30, are positioned within a body lumen 50, e.g. a blood vessel, wherein the catheter 30 with the stent 2 are advanced and positioned within a lumen obstruction 54, typically a partial obstruction or occlusion. As shown in FIG. 3A, the stent 2, having an initial diameter (i.e., a balloon 32 of the catheter 30 is deflated), is preferably positioned within the obstructed lumen.

Figure 3B:
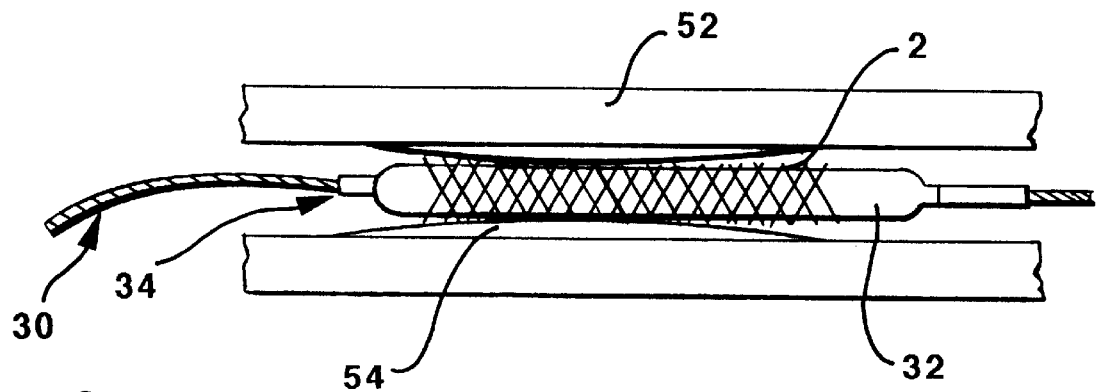
Figure 3C:
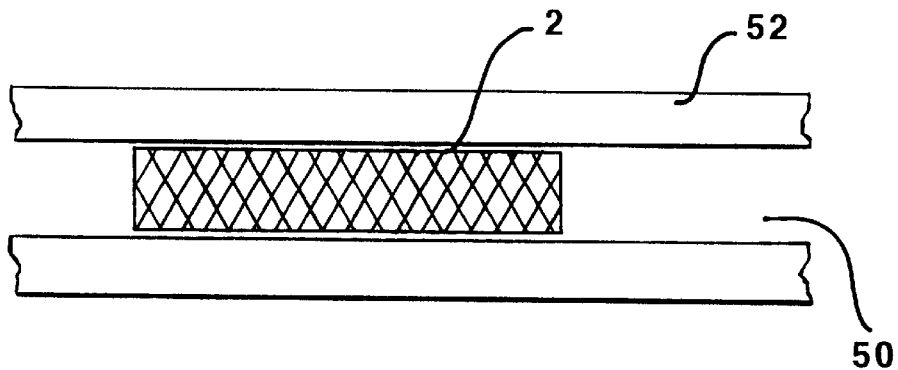

Once in place (i.e., within an obstruction of the body lumen), the balloon 32 is inflated using standard angioplasty procedures and techniques. As the balloon 32 expands, the stent 2 expands from the initial diameter to a second (expanded) diameter, as shown in FIG. 3B. The expanding balloon 32 together with the stent 2 contact the lumen obstruction 54 and expands the body lumen 50. As shown in FIG. 3C, with the angioplasty procedure completed, the balloon 32 is deflated and withdrawn leaving the stent 2 firmly implanted within the body lumen 50. Thus, the previously occluded body lumen 50 is now supported by the stent 2 and patency is restored.

Figure 4:
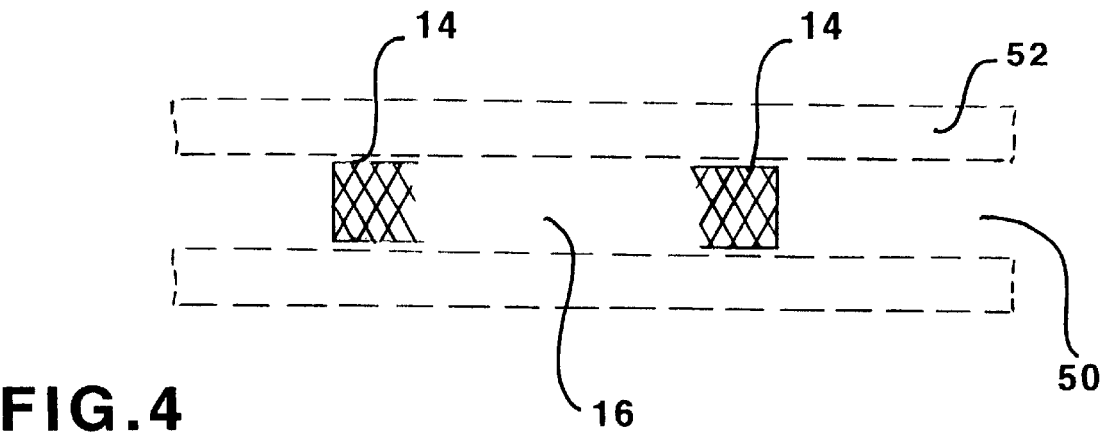
FIG. 4 is a schematic illustration of an implantable device of the present invention in vivo when viewed by x-ray radiation.
Figure 5:
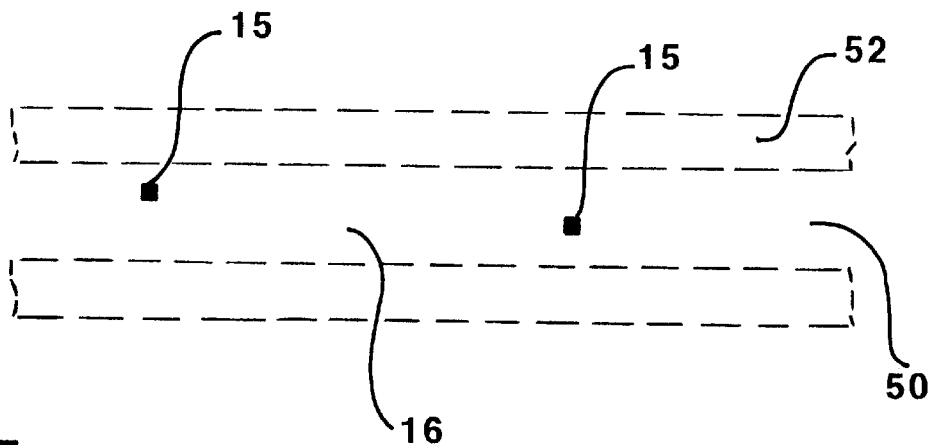
FIG. 5 is a schematic illustration of a conventional stent in vivo when viewed by x-ray radiation.

Once in position, the placement of the stent 2 is typically evaluated and/or monitored by exposure of the body area to x-ray radiation. Placement of a stent 2 in accordance with the present invention can be more accurately assessed because the substantially radiopaque ends of the stent can be viewed by x-ray regardless of the position of the end relative to the line of exposure of the x-ray. As depicted in FIG. 4, substantially radiopaque ends 14 are readily visible upon exposure to x-ray. By contrast, FIG. 5 depicts the visibility of a conventional stent upon exposure to x-ray, which typically includes what is known in the art as "common point" or "dot" markers. The substantially radiopaque ends included in an implantable device in accordance with the present invention are readily visible regardless of the viewing angle whereas the viewing angle may interfere with the visibility of the dot markers. Such interference can be significant to the extent as to be totally invisible, thus defeating the very purpose of including such radiopacity in an implantable device.

Further, because the substantially radiopaque ends can indicate the diameter of the implantable device, a physician may more accurately evaluate an appropriate stent size for a patient. Moreover, also because the substantially radiopaque ends are visible in x-ray as a three dimensional structure and the physician may determine orientation of the stent within the body lumen, the orientation of the lumen itself may also be determined.

The preceding specific embodiments are illustrative of the practice of the invention. The complete disclosures of all patents, patent applications, and publications are incorporated herein by reference as if individually incorporated. Various modifications and alterations of this invention will become apparent to those skilled in the art without departing from the scope and spirit of this invention, and it should be understood that this invention is not to be unduly limited to illustrative embodiments set forth herein.

No. Component
2 implantable device
4 tubular member
4' tubular member
6 longitudinal elements
8 horizontal elements
9 helically wound element
10 perforations
12 device interior
14 first substantially radiopaque end
14' second substantially radiopaque end
15 substantially radiopaque marker of conventional stent
16 radiolucent midsection
16' radiolucent midsection
18 attachment point
20 mandrel
24 first substantially radiopaque end
24' second substantially radiopaque end
28 attachment point
30 catheter
32 balloon
50 body lumen
52 lumen walls
54 lumen obstruction

What is claimed is:

1. An implantable medical device, comprising:
    a radiolucent tubular structure having a first end and a second end, the tubular structure being expandable from an initial diameter to a second diameter; and
    a tubular end structure being formed of a plurality of longitudinal elements and a plurality of horizontal connecting elements and having a first end and a second end, wherein the first end of the tubular end structure is connected to the first end of the radiolucent tubular structure, the tubular end structure being expandable from an initial diameter to a second diameter to provide a substantially uninterrupted passageway therethrough, wherein the tubular end structure consists of a radiopaque material viewable upon exposure to x-ray as a three dimensional structure.

2. The implantable medical device of claim 1 further comprising a second tubular end structure attached to the second end of the tubular structure, the second tubular end structure being expandable from an initial diameter to a second diameter to provide a substantially uninterrupted passageway therethrough, wherein the second tubular end structure comprises a radiopaque material.

3. The implantable device of claim 1 wherein the radiopaque material is more compliant than the radiolucent material.

4. The implantable device of claim 1 wherein the radiopaque material has a density of about 19.3 gm/cm$^3$ to about 21.0 gm/cm$^3$.

5. The implantable device of claim 1 wherein the radiopaque material is selected from the group consisting of tantalum, gold, iridium, and a combination thereof.

6. The implantable device of claim 1 wherein the radiolucent midsection is formed from a material selected from the group of stainless steel, niobium, titanium, and a combination thereof.

7. The implantable device of claim 1 wherein the first tubular structure comprises less than about 25% of a total length of the implantable device.

8. An implantable medical device, comprising:
    a tubular structure having a first end and a second end, the tubular structure being expandable from an initial diameter to a second diameter, wherein the tubular structure is formed from a radiolucent material;
    a first tubular end structure being formed of a plurality of longitudinal elements and a plurality of horizontal connecting elements and having a first end and a second end, wherein the first end of the first tubular end structure is connected to the first end of the tubular structure, the first tubular end structure being expandable from an initial diameter to a second diameter; and
    a second tubular end structure being formed of a plurality of longitudinal elements and a plurality of horizontal connecting elements and having a first end and a second end, wherein the first end of the second tubular end structure is connected to the second end of the tubular structure, the second tubular end structure being expandable from an initial diameter to a second diameter to provide a substantially uninterrupted passageway from the first tubular end structure to the second tubular end structure, wherein the first and the second tubular end structures each consist of a radiopaque material.

9. The implantable device of claim 8 wherein the radiopaque material is more compliant than the radiolucent material.

10. The implantable device of claim 8 wherein the radiopaque material has a density of about 19.3 gm/cm$^3$ to about 21.0 gm/cm$^3$.

11. The implantable device of claim 8 wherein the radiopaque material is selected from the group consisting of tantalum, gold, iridium, and a combination thereof.

12. The implantable device of claim 8 wherein the radiolucent material is selected from the group of stainless steel, niobium, titanium and a combination thereof.

13. The implantable device of claim 8 wherein the first tubular structure and the second tubular structure each comprise less than about 25% of a total length of the implantable device.

14. The implantable device of claim 8 wherein the first tubular structure and the second tubular structure each comprise about 20% to about 15% of a total length of the implantable device.

15. An implantable medical device, comprising:

a radiolucent tubular structure having a first end and a second end, the tubular structure being expandable from an initial diameter to a second diameter; and a tubular end structure having a first end and a second end, wherein the first end of the first tubular end structure is connected to the first end of the radiolucent tubular structure, the tubular end structure being expandable from an initial diameter to a second diameter to provide a substantially uninterrupted passageway therethrough and being 15% to 20% of a total length of the implantable device, wherein the tubular end structure consists of a radiopaque material viewable upon exposure to x-ray as a three dimensional structure.

16. An implantable medical device, comprising:

a tubular structure having a first end and a second end, the tubular structure being expandable from an initial diameter to a second diameter, wherein the tubular structure is formed from a radiolucent material;

a first tubular end structure having a first end and a second end, wherein the first end of the first tubular end structure is connected to the first end of the tubular structure, the first tubular end structure being expandable from an initial diameter to a second diameter and being 15% to 20% of a total length of the implantable device; and a second tubular end structure having a first end and a second end, wherein the first end of the second tubular end structure is connected to the second end of the tubular structure, the second tubular end structure being expandable from an initial diameter to a second diameter to provide a substantially uninterrupted passageway from the first tubular end structure to the second tubular end structure and being 15% to 20% of a total length of the implantable device, and wherein the first and the second tubular end structures each consist of a radiopaque material.

* * * * *

UNITED STATES PATENT AND TRADEMARK OFFICE
CERTIFICATE OF CORRECTION

PATENT NO. : 6,340,368 B1
DATED : January 22, 2002
INVENTOR(S) : Marcel A. E. Verbeek It is certified that error appears in the above-identified patent and that said Letters Patent is hereby corrected as shown below:

Title page,
Item [75], Inventor, delete "Marcel A. E Verbeck" and insert -- Marcel A. E. Verbeek --.
Item [56], References Cited, U.S. PATENT DOCUMENTS, delete "4,430,086" and insert -- 4,430,083 --.
FOREIGN PATENT DOCUMENTS, delete "WO 0 421 729" and insert -- EP 0 421 729 --.

Signed and Sealed this

Sixth Day of July, 2004

JON W. DUDAS
*Acting Director of the United States Patent and Trademark Office*